United States Patent
Atef Ayoub et al.

(10) Patent No.: US 12,425,235 B2
(45) Date of Patent: Sep. 23, 2025

(54) IDENTIFICATION AND AUTHENTICATION OF MULTIPLE CONTROLLERS

(71) Applicant: Thirdwayv, Inc., Irvine, CA (US)

(72) Inventors: Michael Atef Ayoub, Irvine, CA (US); Nabil Wasily, Foothill Ranch, CA (US)

(73) Assignee: THIRDWAYV, INC., Irvine, CA (US)

( * ) Notice: Subject to any disclaimer, the term of this patent is extended or adjusted under 35 U.S.C. 154(b) by 218 days.

(21) Appl. No.: 18/036,159

(22) PCT Filed: Nov. 10, 2021

(86) PCT No.: PCT/US2021/058855
§ 371 (c)(1),
(2) Date: May 9, 2023

(87) PCT Pub. No.: WO2022/103890
PCT Pub. Date: May 19, 2022

(65) Prior Publication Data
US 2023/0403163 A1    Dec. 14, 2023

Related U.S. Application Data

(60) Provisional application No. 63/111,800, filed on Nov. 10, 2020.

(51) Int. Cl.
*H04L 9/32* (2006.01)
*G06F 21/33* (2013.01)
(Continued)

(52) U.S. Cl.
CPC ............ *H04L 9/3263* (2013.01); *G06F 21/33* (2013.01); *G06F 21/44* (2013.01); *G06F 21/602* (2013.01);
(Continued)

(58) Field of Classification Search
None
See application file for complete search history.

(56) References Cited

U.S. PATENT DOCUMENTS

| | | | |
|---|---|---|---|
| 9,684,772 B2 * | 6/2017 | Kuno | G11B 20/10 |
| 10,341,866 B1 * | 7/2019 | Spencer | G06F 21/602 |

(Continued)

FOREIGN PATENT DOCUMENTS

| | | |
|---|---|---|
| KR | 1020150043150 A | 4/2015 |
| KR | 101531662 B1 | 6/2015 |

(Continued)

OTHER PUBLICATIONS

International Search Report and Written Opinion for International PCT Patent Publication No. PCT/US2021/058855, filed Nov. 10, 2021.

(Continued)

*Primary Examiner* — Ali H. Cheema
(74) *Attorney, Agent, or Firm* — Snell & Wilmer LLP

(57) ABSTRACT

Systems, methods and devices to identify and authenticate controllers of embedded devices without direct connection to a server. The system has a plurality of controllers including a first controller and a second controller. The system has an embedded device configured to obtain a first device certificate from the first controller, obtain a second device certificate from the second controller, extract a first user identifier and a first set of device control privileges from the first device certificate, extract a second user identifier and a second set of device control privileges from the second device certificate, determine whether the second user identifier within the second device certificate is the same as to the first user identifier within the first device certificate, and allow or prevent access to the embedded device by the second controller based on the determining whether the second user identifier is the same as the first user identifier.

7 Claims, 10 Drawing Sheets

(51) Int. Cl.
*G06F 21/44* (2013.01)
*G06F 21/60* (2013.01)
*H04L 9/40* (2022.01)

(52) U.S. Cl.
CPC .... *G06F 2221/2143* (2013.01); *H04L 9/3268* (2013.01); *H04L 63/0823* (2013.01); *H04L 63/083* (2013.01); *H04L 63/10* (2013.01); *H04L 63/126* (2013.01)

(56) References Cited

U.S. PATENT DOCUMENTS

| | | |
|---|---|---|
| 10,521,581 B1 | 12/2019 | Anjali et al. |
| 2002/0026581 A1* | 2/2002 | Matsuyama ......... H04L 63/126 713/168 |
| 2006/0041760 A1* | 2/2006 | Huang ................. G06F 21/552 713/189 |
| 2015/0188910 A1* | 7/2015 | Tsai ..................... G06F 21/335 726/1 |
| 2016/0171206 A1* | 6/2016 | Von Bokern ......... H04L 9/3226 726/1 |
| 2017/0048212 A1 | 2/2017 | Everhart et al. |
| 2018/0278613 A1 | 9/2018 | Ganda |

FOREIGN PATENT DOCUMENTS

| | | | |
|---|---|---|---|
| WO | WO-0182038 A2 * | 11/2001 | ............. G06F 21/33 |
| WO | 2014/039142 A1 | 3/2014 | |
| WO | 2016/060742 A1 | 4/2016 | |

OTHER PUBLICATIONS

The Supplementary European search report issued on Sep. 6, 2024 to corresponding European application No. 21892766.3; 5 pages.

\* cited by examiner

IDENTIFICATION AND AUTHENTICATION OF MULTIPLE CONTROLLERS

CROSS-REFERENCE TO RELATED APPLICATIONS

This application is based upon and claims priority to U.S. provisional patent application 63/111,800 entitled "IDENTIFICATION AND AUTHENTICATION OF MULTIPLE CONTROLLERS" and filed Nov. 10, 2020, the entire content of which is incorporated herein by reference.

BACKGROUND

1. Field

The present disclosure is directed to identifying and authenticating controllers, more specifically, the present disclosure is directed to identifying and authenticating multiple controllers to control an Internet-of-Things device.

2. Description of the Related Art

Internet-of-Things (IoT) systems often include an embedded device and a controller. In various instances, multiple controllers may communicate with an embedded device. In prior efforts, each embedded device and each controller communicated with a central control server to selectively authorize or de-authorize access by the controllers to the embedded device and set permissions of each controller for operating the embedded device. However, in various scenarios, communication to a central server is not available. Thus, there remains a need for systems and methods to identify and authenticate controllers of embedded devices without direct connection to a central control server.

SUMMARY

An identification and authentication system is provided. The system may include a plurality of controllers. The plurality of controllers may include a first controller having a first device certificate and a second controller having a second device certificate, the first device certificate having a first user identifier and a first set of device control privileges and the second device certificate having a second user identifier and a second set of device control privileges. The system may include an embedded device. The embedded device may have a memory and a processor. The processor may be configured to obtain, from the first controller, the first device certificate. The processor may be configured to obtain, from the second controller, the second device certificate. The processor may be configured to determine whether the second user identifier within the second device certificate is the same as the first user identifier within the first device certificate and allow or prevent access to the embedded device by the second controller based on the determination.

In various embodiments, the first controller includes a first memory to store a first application, a first user interface to receive the first user identifier and a first user password, and a first network access device to communicate with a server or the embedded device. The first controller may include a first processor coupled to the first user interface and the first network access device. The first processor of the first controller may be configured to send the first user identifier and the first user password to the server, obtain, from the server, the first device certificate, and send the first device certificate to the embedded device.

In various embodiments, the second controller includes a second memory that is configured to store a second application, a second user interface that is configured to receive the second user identifier and a second user password, and a second network access device configured to communicate with the server or the embedded device. The second application is a limited functionality application, or a view-only application and the first application is a fully-functional application that has more privileges than the limited functionality application or the view-only application. The second user identifier is the same as the first user identifier. The second controller may include a second processor coupled to the second user interface and the second network access device. The second processor is configured to send the second user identifier and the second user password to the server, obtain, from the server, the second device certificate associated with the second controller, wherein the second device certificate includes the second user identifier and the second set of device control privileges that is different from the first set of device control privileges, and send the second device certificate to the embedded device.

In various instances the memory of the embedded device is configured to store the first device certificate and the processor of the embedded device is configured to extract the first user identifier and the first set of device control privileges from the first device certificate. Moreover, the processor of the embedded device may be configured to compare the second user identifier with the first user identifier. The processor of the embedded device may be configured to determine that the second user identifier is the same as the first user identifier, obtain the second set of device control privileges from the second device certificate, authenticate access to the embedded device for the second controller even without connectivity to the server, allow access to the embedded device by the second controller based on the second set of device control privileges, and reject or accept commands from the second controller based on the second set of device control privileges. The processor of the embedded device may be configured to prevent access to the embedded device by the second controller when the second user identifier is different from the first user identifier.

The server may be configured to obtain the first user identifier from the first controller when a user logins into a first application on the first controller and the second user identifier from the second controller when the user logins into a second application, generate the first device certificate including binding the first user identifier and the first set of device control privileges to the first device certificate and based on a type of application requesting the first device certificate, generate the second device certificate including binding the second user identifier and the second set of device control privileges to the second device certificate and based on a type of application requesting the second device certificate, digitally sign the first device certificate and the second device certificate using a server signing key, issue the first device certificate to the first controller when the first user identifier and the first user password are authenticated and issue the second device certificate to the second controller when the second user identifier and the second user password are authenticated.

An identification and authentication system is provided. The system may include an embedded device and a plurality of controllers including a primary controller and a secondary controller. The primary controller may include a first memory configured to store a root certificate that includes a first set of device control privileges, and a first processor coupled to the first memory. The first processor may be configured to determine that the first set of device control privileges allow the primary controller to generate a device certificate for the secondary controller, generate the device certificate with a second set of device control privileges, and assign the device certificate to the secondary controller. The first processor may be configured to issue or send the device certificate to the secondary controller and send a public key of the root certificate to the embedded device to verify the device certificate. In various instances, the first processor is configured to digitally sign the device certificate prior to issuing or sending the device certificate to the secondary controller using a private key of the root certificate.

Moreover, the embedded device may have a memory that is configured to store the public key of the root certificate and a processor. The processor of the embedded device may be configured to receive the public key of the root certificate and receive the device certificate. The processor of the embedded device may be configured to determine that the device certificate is valid using the public key of the root certificate to authenticate the secondary controller, and allow the secondary controller to access the embedded device based on the second set of device control privileges when the first set of device control privileges permit access by the secondary controller. To determine that the device certificate is valid the processor of the embedded device may validate a digital signature on the device certificate using public key of the root certificate.

The embedded device may limit operation of the embedded device by the secondary controller based on the second set of device control privileges and limit operations of the embedded device by the primary controller based on the first set of device control privileges, wherein the second set of device control privileges is a subset of the first set of device control privileges. In various instances, the first processor of the primary controller is configured to revoke the device certificate, add the device certificate to a revocation list, and send the revocation list to the embedded device. The processor of the embedded device is configured to determine that the device certificate is invalid based on the revocation list and deny or prevent access to the embedded device by the secondary controller based on the determination.

An identification and authentication system is provided. The system may include a plurality of controllers including a first controller and a second controller and an embedded device. The embedded device may include a memory configured to store a first long-term shared secret and a processor. The processor may be configured to derive a second long-term shared secret using the first long-term shared secret, obtain a third long-term shared secret from the second controller, and authenticate the second controller when the second long-term shared secret matches the third long-term shared secret.

The first controller may include a memory configured to store a first long-term shared secret; and a processor. The processor may be configured to derive the third long-term shared secret using the first long-term shared secret and provide the third long-term shared secret to the second controller.

The second controller may include a memory configured to store the third long-term shared secret, and a processor. The processor may be configured to provide the third long-term shared secret to the embedded device. The processor of the first controller may be configured to derive the third long-term shared secret further using an identifier of the second controller including a Bluetooth Low Energy (BLE) Media-Access-Control (MAC) address or a nonce. The processor of the embedded device may be configured to derive the second long-term shared secret further using the identifier of the second controller and independently of the derivation of the third long-term shared secret derived by the first controller.

Systems, methods, and devices for identifying and authenticating devices include a plurality of controllers and an embedded device. A first controller may grant or deny access of other controllers to the embedded device without a centralized intermediary such as a remote network resource. In this manner, different device control privileges may be set for different devices in the absence of a constant network connection (e.g., continuous in time without interruptions or disconnections) among the devices or between the collection of devices and a network-connected resource such as an authentication server.

BRIEF DESCRIPTION OF THE DRAWINGS

Other systems, methods, features, and advantages of the present invention will be apparent to one skilled in the art upon examination of the following figures and detailed description. Component parts shown in the drawings are not necessarily to scale and may be exaggerated to better illustrate the important features of the present invention.

DETAILED DESCRIPTION

Figure 1:
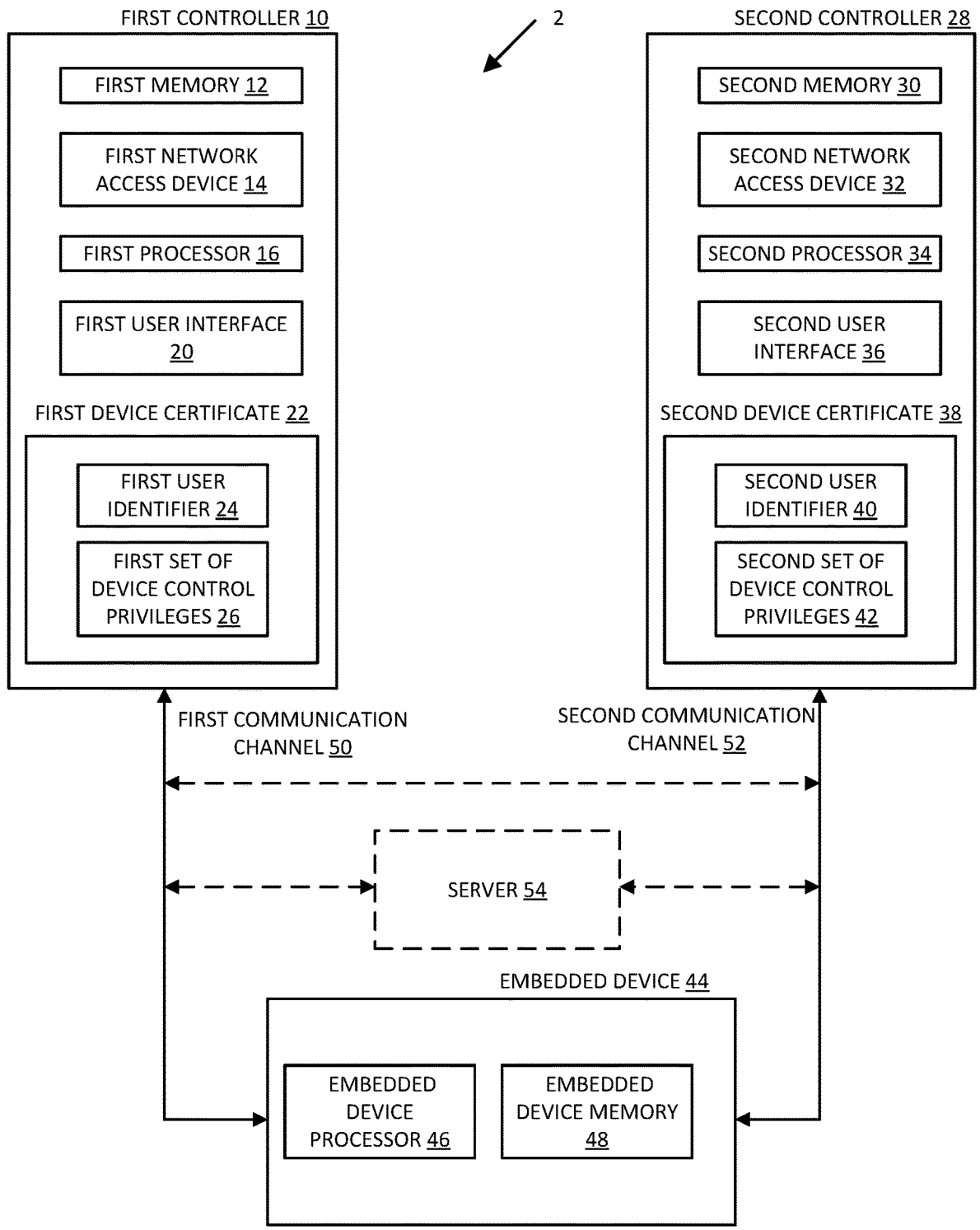
FIG. 1 depicts an identifying and authentication system, in accordance with various embodiments.

As disclosed herein, systems, apparatuses, and methods for identification and authentication are provided.

IoT systems often comprise an IoT device, a controller, and a cloud server. In some embodiments, there is need to enable multiple controllers to control the IoT device simultaneously and/or interchangeably. A controller may be a standalone device or a smartphone application.

For IoT devices that imply a high impact of cybersecurity risks on personal lives or health (e.g. medical devices) the IoT device is required to verify the authenticity of the controller device. When there are multiple controllers, the IoT device not only needs to verify the authenticity but also the ownership of the controllers. For example, an IoT device that is controlled by a first authentic controller may be required to reject a second authentic controller, if both controllers are attributed to different users or if the second authentic controller is attributed to a user without appropriate permissions. Stated differently, the IoT device must verify both the authenticity of the controller and the associated permissions for user associated with the controller.

IoT devices utilized for insulin delivery and glucose monitoring are frequently used in areas without web or internet connectivity. However, such IoT devices may be desired to be controllable by multiple controllers with differing levels of permission, and the identity and nature of the set of multiple controllers may by dynamic. For instance, a diabetic child with an insulin pump controlled by a controller operated by the child's parent may attend school. A school nurse may have a different controller. In a context without reliable internet connectivity, such as a school sports field, a parent may desire to grant authorization to a controller operated by the school nurse to control the insulin pump. The parent may desire to deny authorization for the controller operated by the school nurse to grant further permissions to other controllers operated by coaches, teachers, or other users.

In further instances, an IoT device, such as that utilized for smart home features may be desired to be controllable by multiple controllers with differing levels of permission. For instance, a homeowner with a controller that controls a smart door lock may desire to grant one time permission to a controller operated by a service provider such as a housekeeper.

Current solutions make use of a trusted networks (e.g. a wireless printer on a local network), proximity (e.g. a speaker pairing with a phone), or cloud authentication (e.g. users log in on controllers to an authentication server that is trusted by the IoT device, and authentication server links the IoT device to the user's account). However, these options may not be available for the IoT device when a new controller is introduced to the IoT device. Challenges arise relating to mechanisms to let the IoT device authenticate and attribute multiple controllers to the same user. Challenges also arise relating to mechanisms to assign and enforce different privileges for different controllers. Some controllers may have full control privileges, some controllers may have partial control privileges, and some controllers may have view-only privileges. Some controllers may have no privileges.

The discussions herein provide a mechanism that enables the IoT device (e.g., embedded device) to trust multiple controllers and adopt the privileges of each controller, even if immediate cloud connectivity is not available. For instance, in some cases, each controller is statically assigned user ownership and privileges based on a log-in process and a type of application installed on the controller. Controllers are assigned ownership and privileges prior to communicating with the IoT device. Controllers do not communicate with each other. In other cases, a controller assigns privileges for other controllers. For example, an IoT device may be activated by a first controller (e.g., a primary controller), and accepts secondary controllers that are assigned to it by the primary controllers. In further instances, the first (primary) controller is paired with the IoT device through a first secret, derives a second secret which the IoT can also derive, and delivers this second secret to a second (secondary) controller for use with the IoT device. In various instances, the relationship between the controllers may be limited to one IoT device and the procedure may be repeated with every new IoT device.

Thus, there are various mechanisms to facilitate controllers to control an embedded device without central server control or without always-on network connectivity. A connection to a remote server or other device to identify and authenticate devices is not provided. Rather, controllers directly connect to the embedded device. Controllers may directly connect to the embedded device asynchronously.

The system of identification and authentication may have various architectures. With reference to FIG. 1, an example system of identification and authentication 2 is provided. The system 2 may include a plurality of controllers. In the example, a first controller 10 and a second controller 28 are shown, though any number of controllers may be contemplated. In various instances, the first controller 10 is a primary controller and the second controller 28 is a secondary controller. Stated differently, the first controller 10 may have authority over the second controller 28 and grant or deny access by the second controller 28 to an embedded device 44 as well as establish a level of access (e.g., a set of permitted or denied commands) of the second controller 28 to the embedded device 44.

The first controller 10 and second controller 28 may be similar devices or may be different devices. In various instances, one or more controller is a smartphone, a portable electronic device such as a remote control, a fob, or a handheld transmitter. Moreover, one or more controller may be a Wi-Fi®, ZigBee®, Bluetooth®, or other wired or wireless device. One or more controller may a programmable logic controller (PLC) device, a supervisory control and data acquisition (SCADA) device, or any other device operable to provide commands to other electronic devices.

The system 2 may have an embedded device 44. An embedded device 44 is an electronic device that is controlled by a different electronic device. For instance, an embedded device 44 may be controlled by the first controller 10 and/or the second controller 28. An embedded device 44 may be a medical device, a smart home device, an automation device, an industrial device, or any other electronic device subject to control by other electronic devices. An electronic device may be a Wi-Fi®, ZigBee®, Bluetooth® or other wired or wireless device. One or more embedded device 44 may be a PLC device, a SCADA device, or any other device operable to receive commands form other electronic devices. In various embodiments, a controller and an embedded device 44 may be a same device differently configured.

The first controller 10 may be in communication with the embedded device 44 via a first communication channel 50. The first communication channel 50 may comprise a wired link, a wireless link, or any other mechanism of electronic communication. In various embodiments, the first communication channel 50 is a direct communication channel. In various embodiments, the first communication channel 50 is not through a network but is a direct connection (e.g., wired or wireless connection or link) with the first controller 10 as one endpoint and the embedded device 44 as another endpoint.

The second controller 28 may be in communication with the embedded device 44 via a second communication channel 52. The second communication channel 52 may comprise a wired link, a wireless link, or any other mechanism of electronic communication. In various embodiments, the second communication channel 52 is a direct communication channel. In various embodiments, the second communication channel 52 is not through a network but is a direct connection with the second controller 28 as one endpoint and the embedded device 44 as another endpoint.

In various instances, the first controller 10 and/or second controller 28 may also be in operative electronic communication with a server 54. The server 54 may be a remote computer configured to store, process, and transmit data. For example, the server 54 may be configured to provide certificates, keys, or perform one or more cryptographic function, as will be discussed further herein.

In various instances, the first controller 10 and/or second controller 28 may also be in operative electronic communication with each other via a first communication channel 50 and/or a second communication channel 52.

Having discussed the general architecture of a system of identification and authentication 2, attention is now directed to detailed aspects of the first controller 10. The first controller 10 may include a first memory 12. The first memory 12 may be an electronic memory to store data. The first memory 12 may be a persistent memory, meaning that stored data is retained when power is turned off. The first memory 12 may be a non-persistent memory, meaning that stored data is erased when power is turned off.

The first controller 10 may include a first network access device 14. The first network access device 14 is a communication transceiver configured to send and receive data via the first communication channel 50. The first network access device 14 may be a wired communication device such as a modem or a wireless communication device such as an electromagnetic or optical transceiver.

The first controller 10 may include a first processor 16. The first processor 16 is a computer processor configured to receive, manipulate, and transmit data. The first processor 16 may be a microcontroller, field-programmable gate array, single-board computer, conventional personal computer processor, or any other processor as desired.

The first controller 10 may include a first user interface 20. The first user interface 20 may comprise a display, sound device, one or more light such as one or more LED, or any other human-machine interface as desired. The first user interface 20 may comprise an application running on another device, or operative across a communication link. For instance, the first user interface 20 may be a smartphone application running and/or displayed on a smartphone in operative communication with the first controller 10. Thus, one may appreciate that one or more aspect of the first controller 10 may be distributed, meaning it may be operating on or in concert with another device. In further instances, the first controller 10 is a smartphone and the first user interface 20 is a smartphone application.

The first controller 10 may include a first device certificate 22. A first device certificate 22 may be a collection of electronic data associated with an identity and a permission set. For instance, a first device certificate 22 may include a first user identifier 24 corresponding to an identity of a user associated with the first controller 10 and may include a first set of device control privileges 26 associated with the commands a user is permitted or not-permitted to provide. For instance, a user operating the first controller 10 may issue commands to an embedded device 44. These commands must be consistent with the first set of device control privileges 26 and must not exceed the privileges granted to the user identified in the first user identifier 24.

The second controller 28 may also include various aspects similar to those of the first controller 10. For instance, the second controller 28 may include a second memory 30. The second memory 30 may be an electronic memory to store data. The second memory 30 may be a persistent memory, meaning that stored data is retained when power is turned off. The second memory 30 may be a non-persistent memory, meaning that stored data is erased when power is turned off.

The second controller 28 may include a second network access device 32. The second network access device 32 is a communication transceiver configured to send and receive data via the second communication channel 52. The second network access device 32 may be a wired communication device such as a modem or a wireless communication device such as an electrical, electromagnetic or optical transceiver.

The second controller 28 may include a second processor 34. The second processor 34 is a computer processor configured to receive, manipulate, and transmit data. The second processor 34 may be a microcontroller, field-programmable gate array, single-board computer, conventional personal computer processor, or any other processor as desired.

The second processor 34 may include a second user interface 36. The second user interface 36 may comprise a display, sound device, one or more light such as one or more LED, and/or any other human-machine interface as desired. The second user interface 36 may comprise an application running on another device, or operative across a communication link. For instance, the second user interface 36 may be a smartphone application running and/or displayed on a smartphone in operative communication with the second controller 28. Thus, one may appreciate that one or more aspect of the second controller 28 may be distributed, meaning it may be operating on or in concert with another device. In further instances, the second controller 28 is a smartphone and the second user interface 36 is a smartphone application.

The second controller 28 may include a second device certificate 38. The second device certificate 38 may be a collection of electronic data associated with an identity and a permission set. For instance, the second device certificate 38 may include a second user identifier 40 corresponding to an identity of a user associated with the second controller 28 and may include a second set of device control privileges 42 associated with the commands a user is permitted or not-permitted to provide. For instance, a user operating the second controller 28 may issue commands to an embedded device 44. These commands must be consistent with the second set of device control privileges 42 and must not exceed the privileges granted to the user identified in the second user identifier 40.

Having discussed the general architecture of a system of identification and authentication 2, as well as detailed aspects of the first controller 10 and the second controller 28, attention is now directed to detailed aspects of the embedded device 44. The embedded device 44 may include an embedded device memory 48. The embedded device memory 48 may be an electronic memory to store data. The embedded device memory 48 may be a persistent memory, meaning that stored data is retained when power is turned off. The embedded device memory 48 may be a non-persistent memory, meaning that stored data is erased when power is turned off. The embedded device 44 may include an embedded device processor 46. The embedded device processor 46 is a computer processor configured to receive, manipulate, and transmit data. The embedded device processor 46 may be a microcontroller, field-programmable gate array, single-board computer, conventional personal computer processor, or any other processor as desired. The embedded device may have other aspects, such as sensors or effectors, actuators, motors, relays and the like which may be operable in response to commands provided to the embedded device 44 by the first controller 10 and/or the second controller 28. In various instances, the embedded device 44 is an insulin pump. In various instances, the embedded device 44 is a smart home device such as a smart door lock.

Figure 2A:
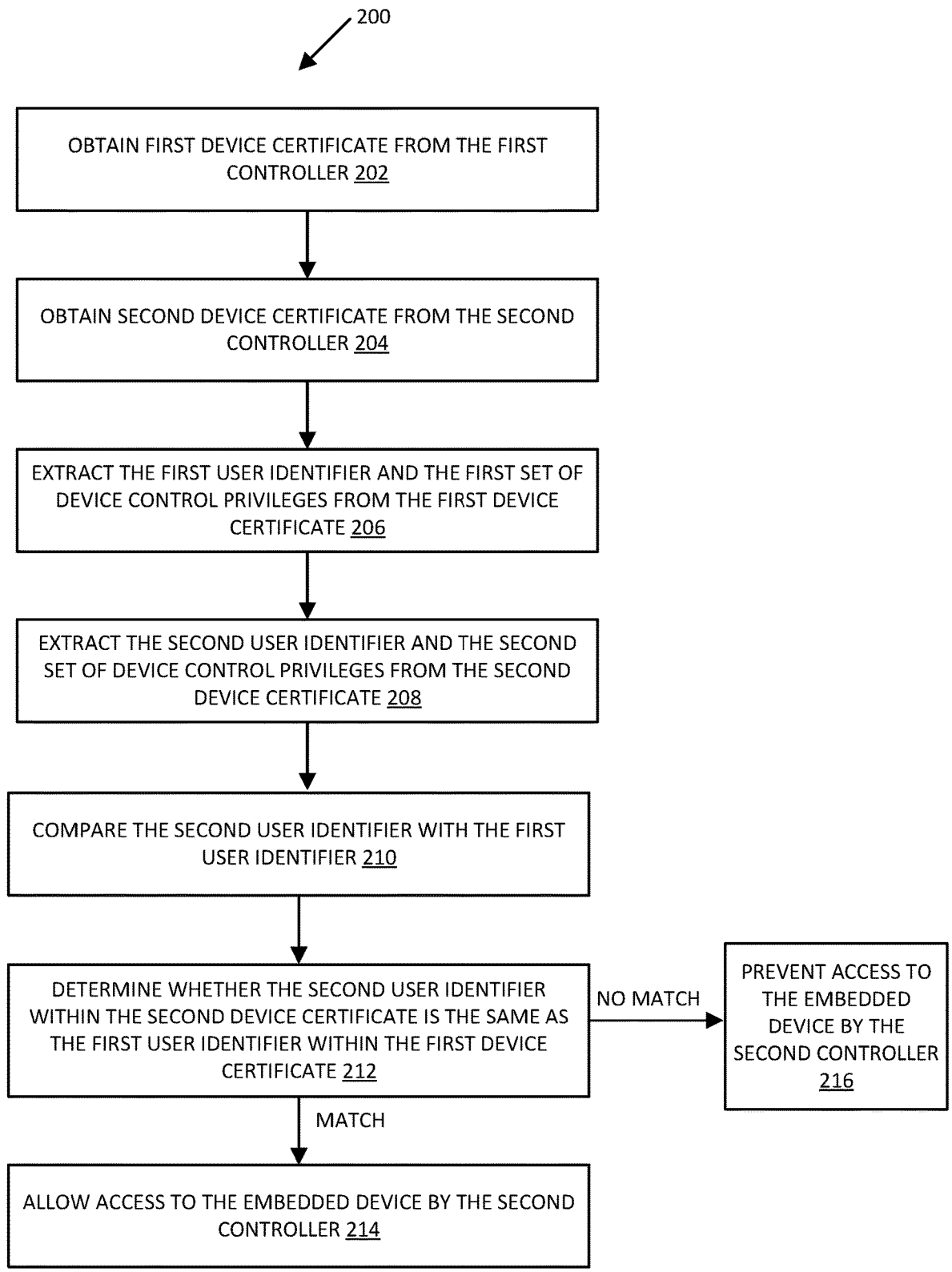
FIG. 2A depicts aspects of an identification and authentication method performed by an embedded device, in accordance with various embodiments.

Attention is now directed to FIG. 2A, with periodic reference to aspects of FIG. 1. FIG. 2A provides an identification and authentication method 200 performed by an embedded device 44. For example, an identification and authentication system 2 may be provided with a plurality of controllers including the first controller 10 and the second controller 28. The first controller 10 may have the first device certificate 22 and the second controller 28 may have the second device certificate 38. The first device certificate 22 may have a first user identifier 24 and a first set of device control privileges 26. The second device certificate 38 may have a second user identifier 40 and a second set of device control privileges 42. The system 2 may additionally include an embedded device 44 with an embedded device processor 46 and an embedded device memory 48.

The embedded device 44 may obtain the first device certificate 22 from the first controller 10 (block 202). For instance, the embedded device 44 may communicate with the first controller 10 via the first communication channel 50. The first controller 10 may, via the first network access device 14, transmit data over the first communication channel 50 that corresponds to the first device certificate 22 from the first controller 10 to the embedded device 44. The embedded device 44 may receive the data and store a representation of the first device certificate 22 in embedded device memory 48.

The embedded device 44 may obtain the second device certificate 38 from the second controller 28 (block 204). For instance, the embedded device 44 may communicate with the second controller 28 via the second communication channel 52. The second controller 28 may, via the second network access device 32, transmit data over the second communication channel 55 that corresponds to the second device certificate 38 from the second controller 28 to the embedded device 44. The embedded device 44 may receive the data and store a representation of the second device certificate 38 in embedded device memory 48.

The embedded device 44 may extract the first user identifier 24 and first set of device control privileges 26 from the first device certificate 22 (block 206). For instance, the embedded device processor 46 may load the first device certificate 22 from the embedded device memory 48, and may process the first device certificate 22 to separate the data representing the first user identifier 24 and the data representing the first set of device control privileges 26.

The embedded device 44 may extract the second user identifier 40 and second set of device control privileges 42 from the second device certificate 38 (block 208). For instance, the embedded device processor 46 may load the second device certificate 38 from the embedded device memory 48, and may process the second device certificate 38 to separate the data representing the second user identifier 40 and the data representing the second set of device control privileges 42.

The embedded device 44 may compare the second user identifier 40 to the first user identifier 24 (block 212). If the first user identifier 24 and the second user identifier 40 do not match, then the embedded device 44 may prevent access to the embedded device 44 by the second controller 28 (block 216). Specifically, the embedded device processor 46 may reject commands from the second controller 28 and/or refrain from processing communication from the second controller 28 or storing data from the second controller 28 in the embedded device memory 48.

If the first user identifier 25 and the second user identifier 40 do match, then the embedded device 44 may allow access to the embedded device 44 by the second controller 28 (block 214). Specifically, then embedded device 44 may accept commands from the second controller 28 and/or process communication from the second controller 28 or store data from the second controller 28 in the embedded device memory 48.

Figure 2B:
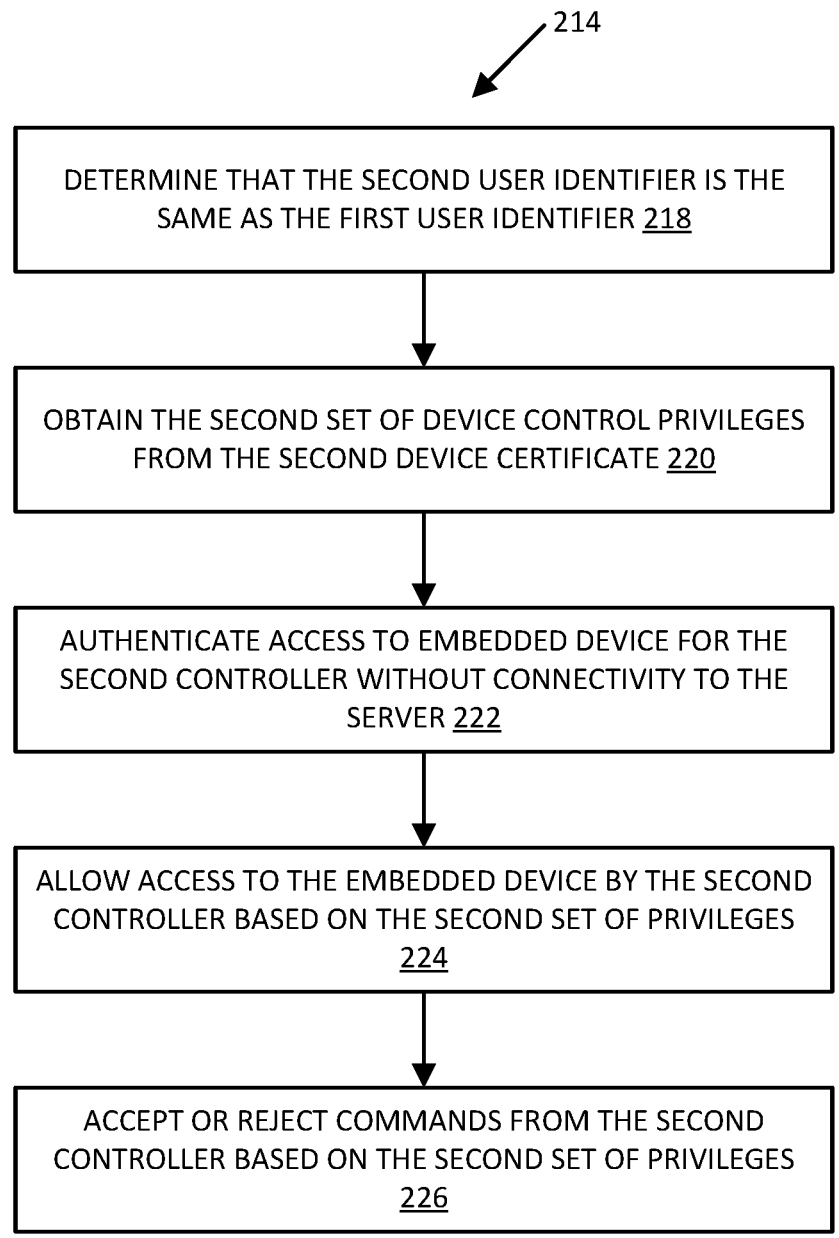
FIG. 2B depicts aspects of allowing access to the embedded device performing the method of FIG. 2A, in accordance with various embodiments.

Continuing with reference to FIGS. 1 and 2A, additional reference is directed to FIG. 2B for a detailed discussion of allowing access to the embedded device 44 by the second controller 28 in block 214. For instance, this access may be limited according to various permissions. For instance, a user of the second controller 28 may have rights to issue some commands to the embedded device 44 but not other commands. For instance, the user may have rights to issue commands causing the embedded device 44 to run a preapproved program to move an actuator, take a measurement, record data, etc., but may be limited from running an actuator past a programmed stop point, changing measurement values, or deleting data.

Thus, allowing such access may include further aspects. For instance, the embedded device 44 may determine that the second user identifier 40 is the same as the first user identifier 24 (block 218). The processor of the embedded device 44 may load data representing the first user identifier 24 and data representing the second user identifier 40. In response to the user identifiers being the same, then it may be assumed that the users associated with the first user identifier 24 and the second user identifier 40 are the same user.

The embedded device 44 may obtain the second set of device control privileges 42 from the second device certificate 38 (block 220). The embedded device 44 may then authenticate access to the embedded device 44 for the second controller 28 without connectivity to a server 54 (block 222). The embedded device 44 thus will grant access to resources associated with the embedded device 44, such as the embedded device processor 46 and/or the embedded device memory 48.

However, this access may be less than unlimited. For instance, the embedded device 44 may allow access to the embedded device 44 by the second controller 28 based on the second set of privileges (block 224). Notably, while the first user identifier 24 and the second user identifier 40 may be the same, the first set of privileges and the second set of privileges may be different. For instance, the first set of privileges may include the privilege to authenticate access to the embedded device 44 for other controllers (as is being performed in this instant description), but the second set of device control privileges 42 may omit such a privilege (such as to limit the proliferation of access among users).

The embedded device 44 may accept or reject commands from the second controller 28 based on the second set of privileges (block 226).

The discussion of a method of identification and authentication 200 performed by an embedded device 44 should also include a discussion of steps performed by the first controller 10 in connection with the identification and the authentication. In various instances, one or more of these aspects may be performed in parallel with aspects performed by the embedded device 44. One or more of these aspects may be performed before or after aspects performed by the embedded device 44.

Figure 3:
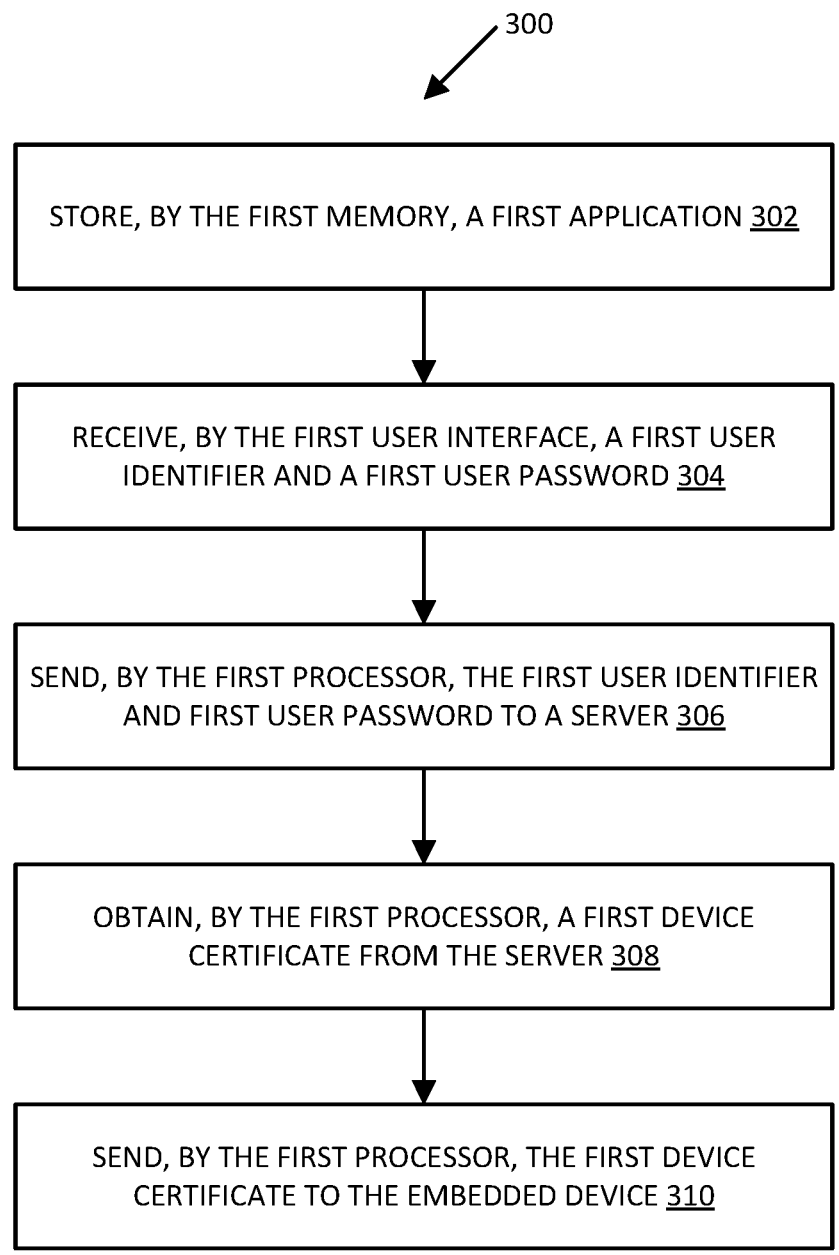
FIG. 3 depicts aspects of the identification and authentication method performed by a first controller, in accordance with various embodiments.

Thus, with reference to FIG. 1 and FIG. 3, the method of identification and authentication 200 (FIG. 2A) may also include a sub-method, such as a method of establishing a device certificate by a first controller 300. In various embodiments, the method of establishing the device certificate by the first controller 300 (and thus the method of identification and authentication 200) may include storing, by the first memory 12 of the first controller 10, a first application (block 302). The first application may provide for entry by a user of the first controller 10, a first user identifier 24 and a first user password. The first user identifier 24 may be a sequence of keypresses, a sequence of touch screen keypresses, a biometric identifier such as facial recognition, fingerprint recognition, or other recognitions. The first user password may be a sequence of keypresses, a sequence of touch screen keypresses, a biometric identifier such as facial recognition, fingerprint recognition, or other recognitions.

The user may enter the first user identifier 24 and the first user password into fields provided by the first application on the first user interface 20 of the first controller 10. Thus, the method may include receiving, by the first user interface 20, a first user identifier 24 and a first user password (block 304).

The first processor 16 of the first controller 10 may send the first user identifier 24 and the first user password to the server 54 (block 306). For instance, the first controller 10 may transmit data representing the first user identifier 24 and the first user password via the first communication channel 50 from the first network access device 14 of the first controller 10 to the server 54. The server 54 may receive the data representative of the first user identifier 24 and the first user password and generate a device certificate based on the first user identifier 24 and the first user password. The server 54 may perform cryptographic or other calculations based on at least one of the first user identifier 24 and the first user password to generate the device certificate. Thus, the first controller 10 may obtain, by the first processor 16, a first device certificate 22 from the server 54 (block 308). This first device certificate 22 may correspond to the first user identifier 24 and the first user password and may be useful for performing the method of identification and authentication 200 as discussed previously. Consequently, the first processor 16 may send the first device certificate 22 to the embedded device 44 (block 310). Referring back to FIG. 2A, and in particular block 202, one may appreciate that block 310 may occur prior to block 202 ("obtaining a first device certificate 22 from the first controller 10").

Figure 4:
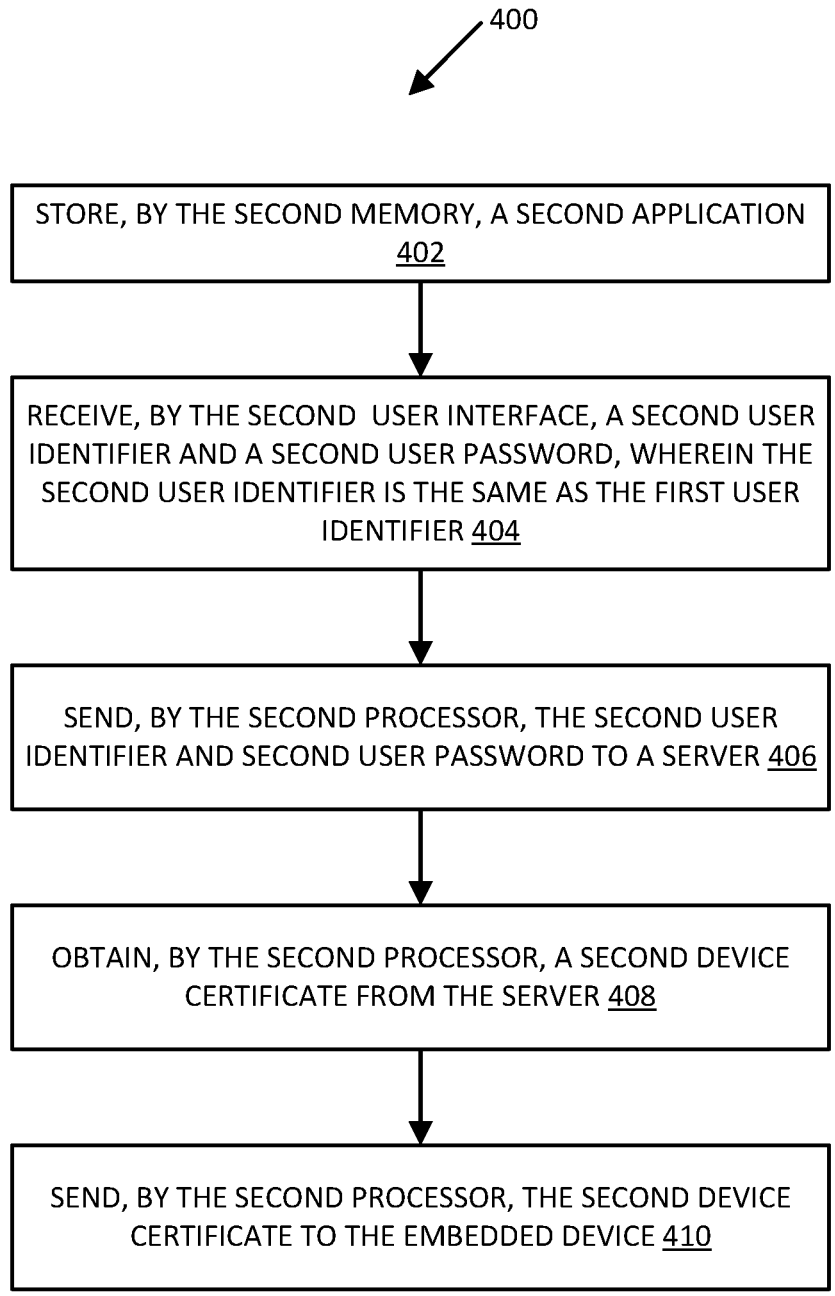
FIG. 4 depicts aspects of the identification and authentication method performed by a second controller, in accordance with various embodiments.

Turning attention from the first controller 10 to the second controller 28, FIG. 4 provides a sub-method performed by the second controller 28. One may recall that block 204 of FIG. 2A provides for obtaining a second device certificate 38 from the second controller 28. In various instances, the method of identification and authentication 200 (FIG. 2A) includes a sub-method, such as a method of establishing a device certificate 400 performed by a second controller 28. In various embodiments, the method 400 of establishing the device certificate by the second controller 28 (and thus the method of identification and authentication 200) may include storing, by the second memory 30 of the second controller 28, a second application (block 402). Notably, the second application may be a limited functionality application or a view-only application, while the first application is a fully-functional application that has more privileges than the limited functionality application or the view-only application. However, the interoperation of the first controller 10 and the second controller 28 with the embedded device 44 according to the method of identification and authentication 200 facilitates identification and authentication of the second controller 28, without requiring the full functionality or full privileges associated with the application on the first controller 10. In this manner, identification and authentication of the second controller 28 may proceed without exposing the entire feature set of the first application to the user of the second controller 28. This improves system security by limiting distribution of the first application.

The method 400 of establishing the device certificate by the second controller 28 may proceed with receiving, by the second user interface 36, a second user identifier 40 and the second user password, wherein the second user identifier 40 is the same as the first user identifier 24 (block 404).

The second application may provide for entry by the user of the second controller 28 of the second user identifier 40 and the second user password. The second user identifier 40 may be a sequence of keypresses, a sequence of touch screen keypresses, a biometric identifier such as facial recognition, fingerprint recognition, or other recognitions. The second user password may be a sequence of keypresses, a sequence of touch screen keypresses, a biometric identifier such as facial recognition, fingerprint recognition, or other recognitions. The user may enter the second user identifier 40 and the second user password into fields provided by the first application on a first user interface 20 of the first controller 10.

The second processor 34 of the second controller 28 may send the second user identifier 40 and the second user password to the server 54 (block 406). For instance, the second controller 28 may transmit data representing the second user identifier 40 and the second user password via the second communication channel 52 from the second network access device 32 of the second controller 28 to the server 54. The server may receive the data representative of the second user identifier 40 and the second user password and generate a device certificate based on the second user identifier 40 and the second user password. The server may perform cryptographic or other calculations based on at least one of the second user identifier 40 and the second user password to generate the device certificate. Thus, the second controller 28 may obtain, by the second processor 34, a second device certificate 38 from the server 54 (block 408). This second device certificate 38 may correspond to the second user identifier 40 and the second user password and may be useful for performing the method of identification and authentication 200 as discussed previously. Consequently, the second processor 34 may send the second device certificate 38 to the embedded device 44 (block 410). Referring back to FIG. 2A, and in particular block 204, one may appreciate that block 410 may occur prior to block 204 ("obtaining a second device certificate 38 from the second controller 28").

Figure 5:
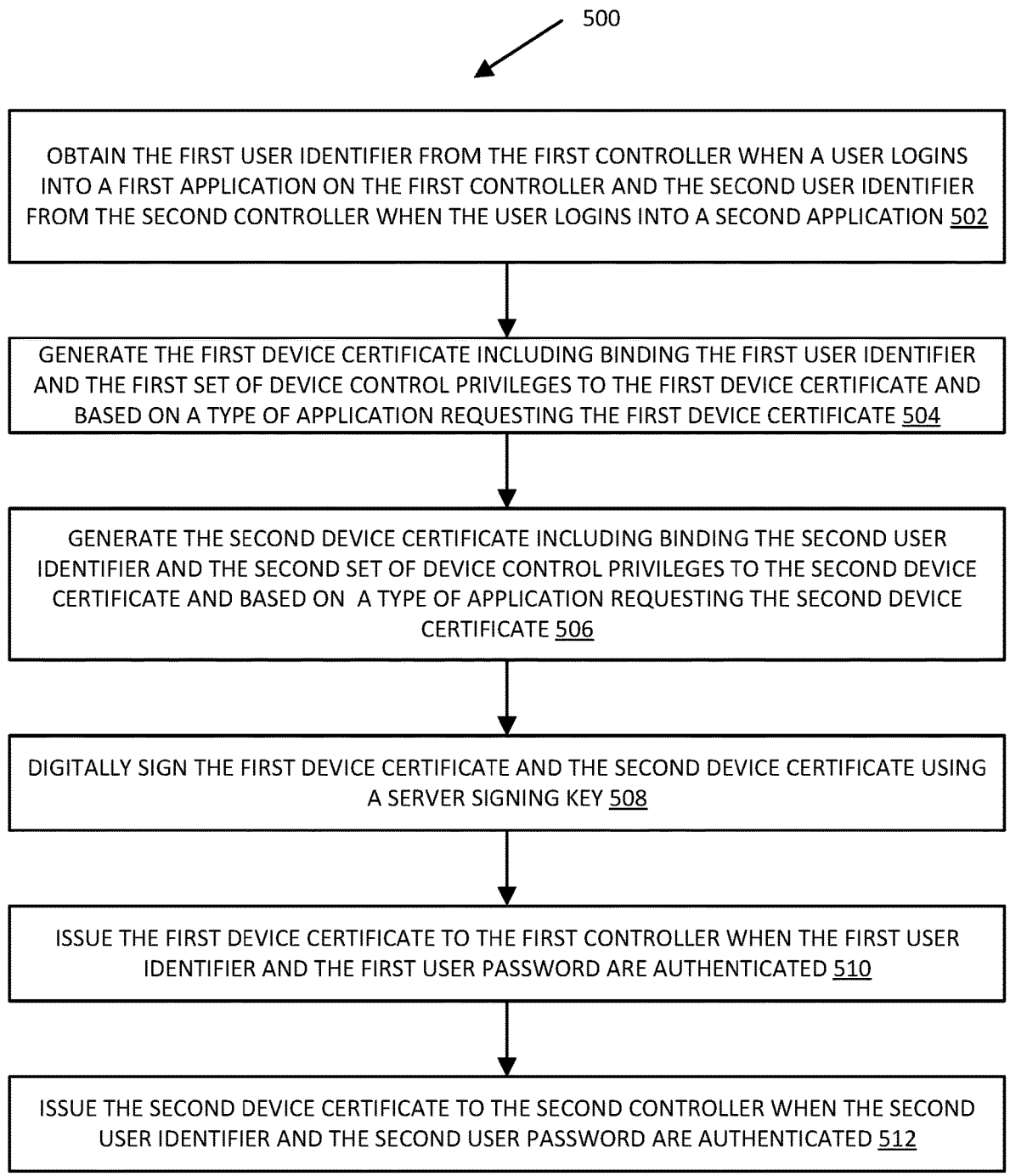
FIG. 5 depicts aspects of the identification and authentication method performed by a server, in accordance with various embodiments.

The server may perform various steps in connection with the communicating with the first controller 10 and the second controller 28 to complete the method 300 of establishing a device certificate performed by a first controller 10 and the method 400 of establishing a device certificate performed by a second controller 28. Thus, with reference to FIGS. 1 and 5, the method of identification and authentication 200 (FIG. 2A) may also include a sub-method, such as a method of generating device certificates 500 by a server 54. In various embodiments, the method 500 (and thus the method of identification and authentication 200) may include obtaining the first user identifier 24 from the first controller 10 when a user logins into a first application on the first controller 10 and the second user identifier 40 from the second controller 28 when the user logins into a second application (block 502). One may appreciate that this aspect corresponds to block 306 (FIG. 3) and block 406 (FIG. 4) performed by the first controller 10 and the second controller 28, respectively.

The server may generate the first device certificate 22. The server may generate the first device certificate 22 by binding the first user identifier 24 and the first set of device control privileges 26 to the first device certificate 22 and based on a type of application requesting the first device certificate 22 (block 504). For instance, a fully featured application (such as the first application) and a limited-feature application (such as the second application) might be associated with different certificate contents.

The server may generate the second device certificate 38. The server may generate the second device certificate 38 by binding the second user identifier 40 and the second set of device control privileges 42 to the second device certificate 38 and based on a type of application requesting the second device certificate 38 (block 506). Again, a fully featured application (such as the first application) and a limited-feature application (such as the second application) might be associated with different certificate contents.

The server may digitally sign the first device certificate 22 and the second device certificate 38. For instance, the server may digitally sign the certificates using a server signing key (block 508). In this manner, the authenticity of device certificates may be established.

The server may issue the first device certificate 22 to the first controller 10 when the first user identifier 24 and the first user password are authenticated (block 510). One may recall that the first processor 16 of the first controller 10 may send the first user identifier 24 and the first user password to the server 54 in block 306 (FIG. 3) and then may obtain, by the first processor 16, a first device certificate 22 from the server in block 308 (FIG. 3). Between these aspects, the server may issue the first device certificate 22. Notably, authenticating the first user identifier 24 and the first user password may include verifying their correctness by the server, or in further instances, may include verifying their correctness by the first controller 10 and indicating this correctness by the first controller 10 to the server.

The server may issue the second device certificate 38 to the second controller 28 when the second user identifier 40 and the second user password are authenticated (block 512). One may recall that the second processor 34 of the second controller 28 may send the second user identifier 40 and the second user password to the server 54 in block 406 (FIG. 4) and then may obtain, by the second processor 34, a second device certificate 38 from the server in block 408 (FIG. 4). Between these aspects, the server 54 may issue the second device certificate 38. Notably, authenticating the second user identifier 40 and the second user password may include verifying their correctness by the server, or in further instances, may include verifying their correctness by the second controller 28 and indicating this correctness by the second controller 28 to the server.

Having discussed the aspects of the method 200 (FIG. 2A) that are performed by each component of the system 2 (FIG. 1), the disclosure now shifts to a discussion of a further embodiment of a method of identification and authentication performable by the system 2. In various embodiments, the system 2 is configured to have a primary controller and a secondary controller. A primary controller may have rights to permit or deny access by secondary controllers to the embedded device 44, while a secondary controller does not have rights to permit or deny access by primary or secondary controllers to the embedded device 44. Stated differently, the primary controller may be termed a "master controller" and the secondary controller may be termed a "slave controller."

Figure 6:
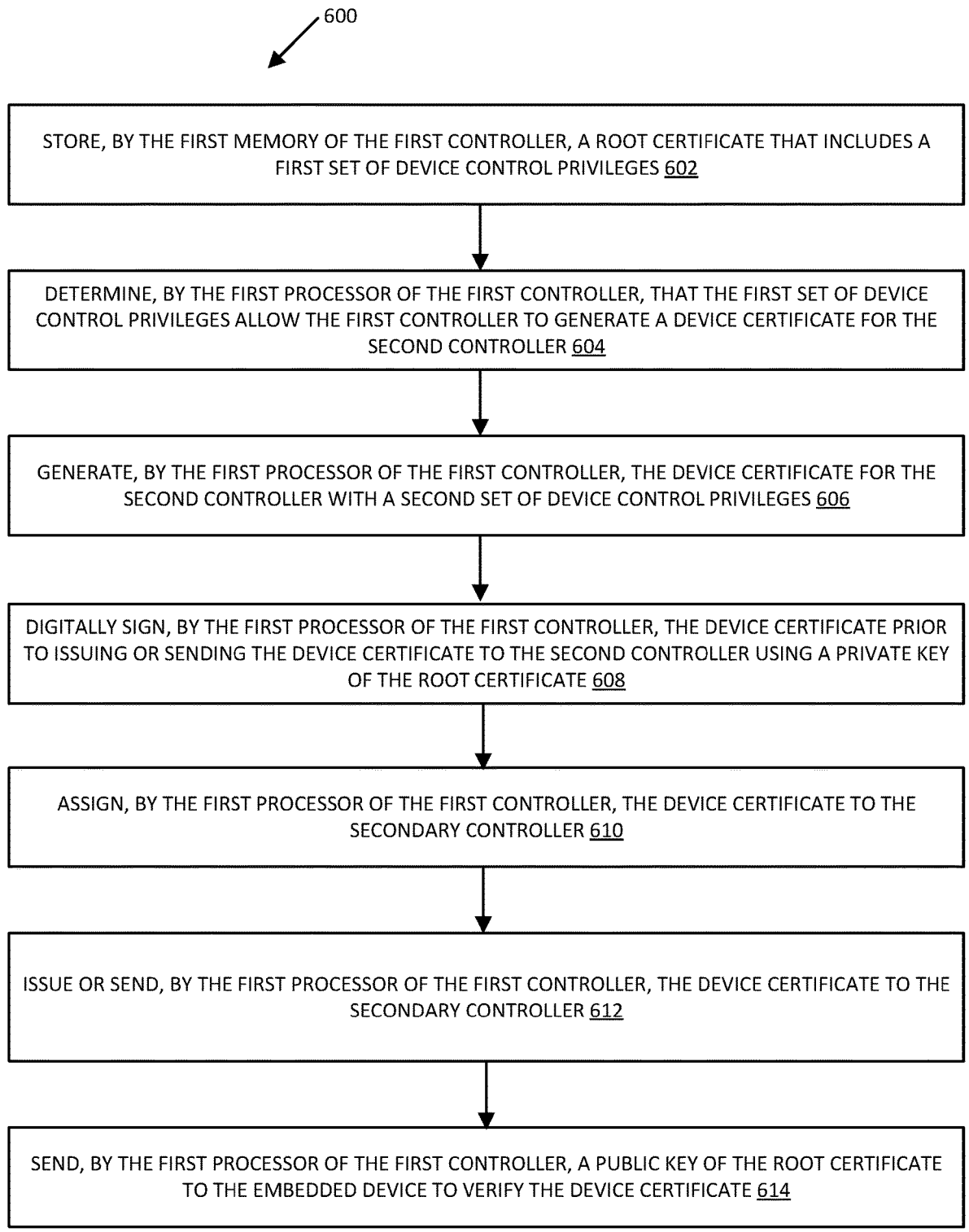
FIG. 6 depicts aspects of an identification and authentication method performed by a first controller having a root certificate, in accordance with various embodiments.

With reference to FIGS. 1 and 6, a method of identification and authentication 600 including a root certificate is disclosed. The method of identification and authentication including a root certificate may include a primary controller and a secondary controller. As used herein, the first controller 10 may be the primary controller and the second controller 28 may be the secondary controller. In various instances, the first memory 12 of the first controller 10 may store a root certificate that includes a first set of device control privileges 26 (block 602). The first processor 16 of the first controller 10 may determine that the first set of device control privileges 26 allow the first controller 10 to generate a second device certificate 38 for the second controller 28 (block 604). In response to this determining, the first processor 16 of the first controller 10 may generate the second device certificate 38 for the second controller 28 with a second set of device control privileges 42 (block 606). The first processor 16 of the first controller 10 may digitally sign the second device certificate 38 prior to issuing or sending the second device certificate 38 to the second controller 28 (block 608). The first processor 16 may utilize a private key of the root certificate to digitally sign the second device certificate 38.

The first processor 16 of the first controller 10 may assign the second device certificate 38 to the second controller 28 (block 610). The first processor 16 of the first controller 10 may issue or send, by the first processor 16 of the first controller 10, the second device certificate 38 to the secondary controller (block 612). For instance, the first processor 16 may utilize the first network access device 14 to send the second device certificate 38 over the first communication channel 50 or second communication channel 52 and to the second controller 28.

In addition, the first processor 16 of the first controller 10 may send a public key of the root certificate to the embedded device 44 to verify the second device certificate 38 (block 614). For instance, when the second controller 28 connects to the embedded device 44, the embedded device 44 can verify that the second controller 28 is authorized to connect to the embedded device 44 by applying the public key of the root certificate to the digitally signed device certificate, because the device certificate was signed using a private key of the root certificate prior to transmission to the second controller 28.

Figure 7:
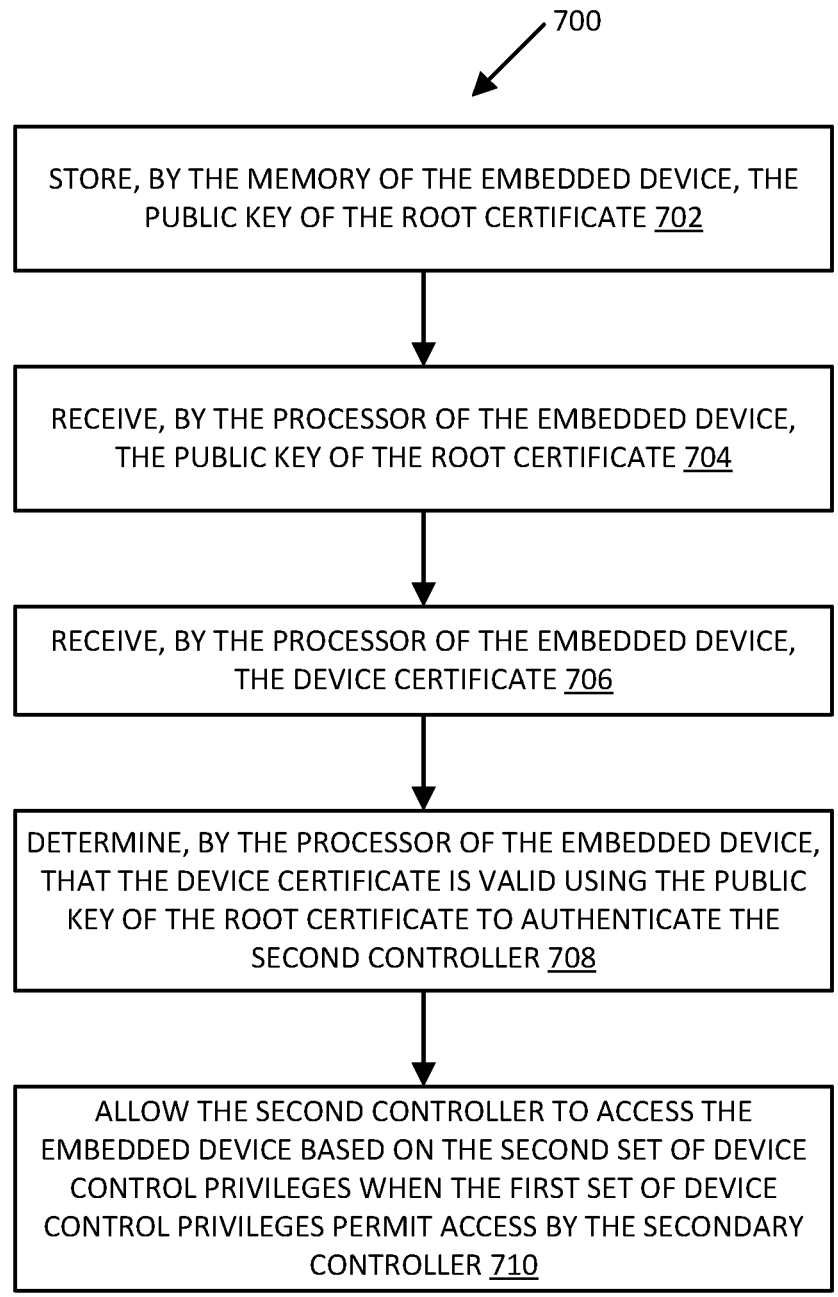
FIG. 7 depicts aspects of an identification and authentication method performed by an embedded device having the root certificate, in accordance with various embodiments.

Turning now to FIGS. 1 and 7, the method of identification and authentication including the root certificate may also include a sub-method performed by the embedded device 44. As mentioned, the embedded device 44 may receive a public key of the root certificate for use to verify the second device certificate 38 (FIG. 6, block 614). Upon receipt of the public key, the embedded device 44 having a key of the root certificate may perform aspects of a sub-method. For instance, a method of root certificate credential verification 700 may be performed. The method of root certificate credential verification 700 may include storing, by a memory of the embedded device 44, the public key of the root certificate (block 702). The method may include receiving, by the embedded device processor 46 of the embedded device 44, the public key of the root certificate from the embedded device memory 48 of the embedded device 44 (block 704). The method may also include receiving, by the embedded device processor 46 of the embedded device 44, the second device certificate 38 from the second controller 28 (block 706).

The embedded device processor 46 of the embedded device 44 may determine that the second device certificate 38 is valid by using the public key of the root certificate to authenticate the second controller 28 (block 708). In various instances, to determine that the device certificate is valid, the embedded device processor 46 is configured to validate a digital signature on the second device certificate 38 by using the public key of the root certificate.

The embedded device processor 46 of the embedded device 44 may allow the second controller 28 to access the embedded device 44 based on the second set of device control privileges 42 when the first set of device control privileges 26 permit access by the secondary controller (block 710). In various embodiments, the embedded device 44 limits operation of the embedded device 44 by the second controller 28 (secondary controller) based on the second set of device control privileges 42 and limits operations of the embedded device 44 by the first controller 10 (primary controller) based on the first set of device control privileges 26. The second set of device control privileges 42 is a subset of the first set of device control privileges 26.

Figure 8:
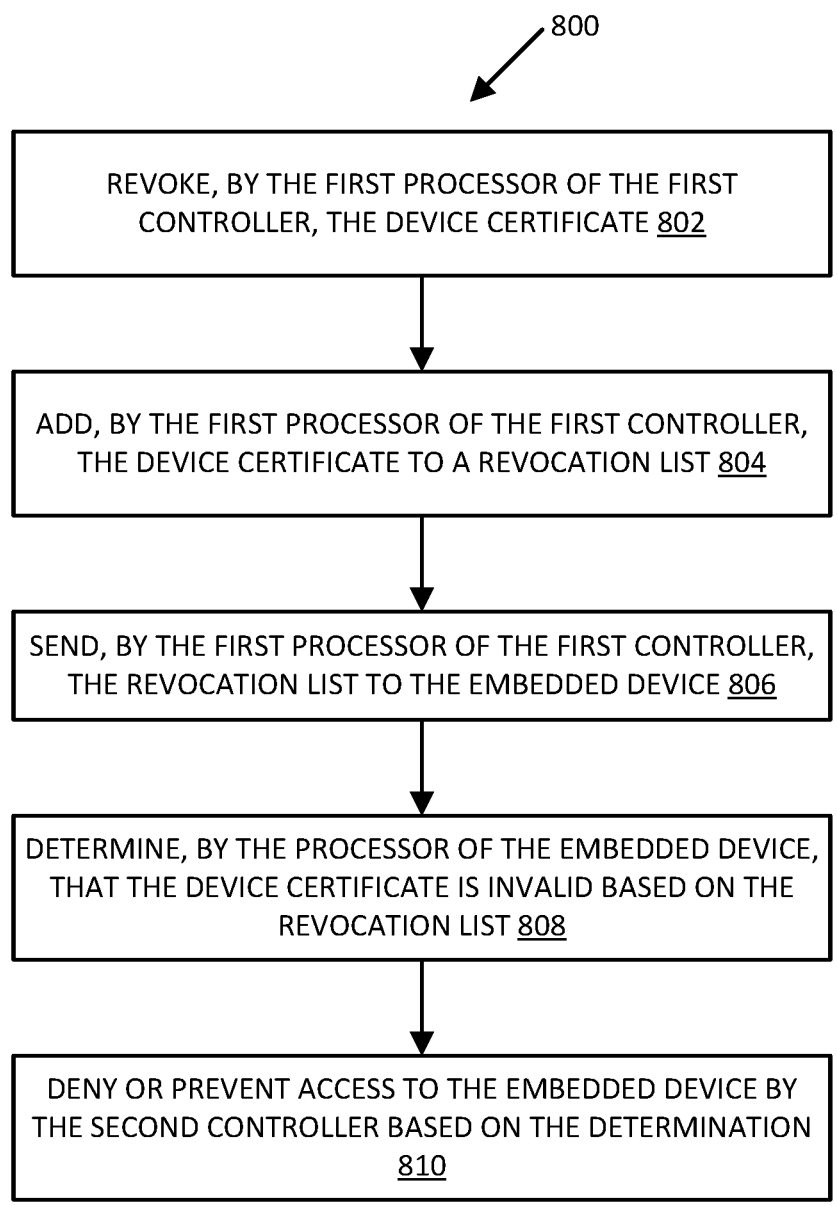
FIG. 8 depicts aspects of an identification and authentication method performed to revoke a device certificate, in accordance with various embodiments.

From time to time, the system 2 may revoke access to the embedded device 44 by a controller that previously had access to the embedded device 44. For instance, ownership of the controller may have changed, or the user of the controller may no longer be desired to have control of the embedded device 44. With reference to FIGS. 1 and 8, a method of device certificate revocation 800 is provided. Notably, the first controller 10 is able to revoke access of the second controller 28 to the embedded device 44 without use of a server 54. Moreover, the first controller 10 is able to revoke access of the second controller 28 without any direct connection between the first controller 10 and the second controller 28. Rather, the first controller 10 is able to revoke access of the second controller 28 to the embedded device 44 via a connection between the first controller 10 and the embedded device 44, with no other connections required. In various embodiments, the method may include revoking, by the first processor 16 of the first controller 10, the second device certificate 38 of the second controller 28 (block 802). The method may include adding, by the first processor 16 of the first controller 10, the second device certificate 38 to a revocation list (block 804). A revocation list may be a list of device certificates that are presently revoked, meaning the device certificates were previously associated with a set of device control privileges, but now are associated with a null set of device control privileges (e.g., no privileges).

The method may include sending, by the first processor 16 of the first controller 10, the revocation list to the embedded device 44 (block 806). The embedded device processor 46 of the embedded device 44 may determine that the second device certificate 38 is invalid based on the revocation list sent to the embedded device 44 by the first controller 10 (block 808). In response to determining that the second device certificate 38 is invalid, the embedded device 44 may deny or prevent access to the embedded device 44 by the second controller 28 (block 810). In various instances, the first controller 10 may be a primary controller and the second controller 28 may be a secondary controller. As such, the first controller 10 may have rights to revoke access of the second controller 28, while the second controller 28 may have no rights to revoke access of the first controller 10. As such, the first controller 10 may facilitate the granting and revoking of rights of the second controller 28 without need for a centralized server or ongoing network access to the Internet or a Cloud network.

Finally, the disclosure now shifts to a discussion of a further embodiment of a method of identification and authentication performable by the system 2. In various instances, the method involves one or more long-term shared secret. A long-term shared secret may comprise a key or other data. The long-term shared secret may have self-referential cryptographic elements to establish the validity of the long-term and ameliorate forgery. In various embodiments, the system 2 is configured to have a primary controller and a secondary controller. A primary controller may have rights to permit or deny access by secondary controllers to the embedded device 44, while a secondary controller does not have rights to permit or deny access by primary or secondary controllers to the embedded device 44.

Figure 9:
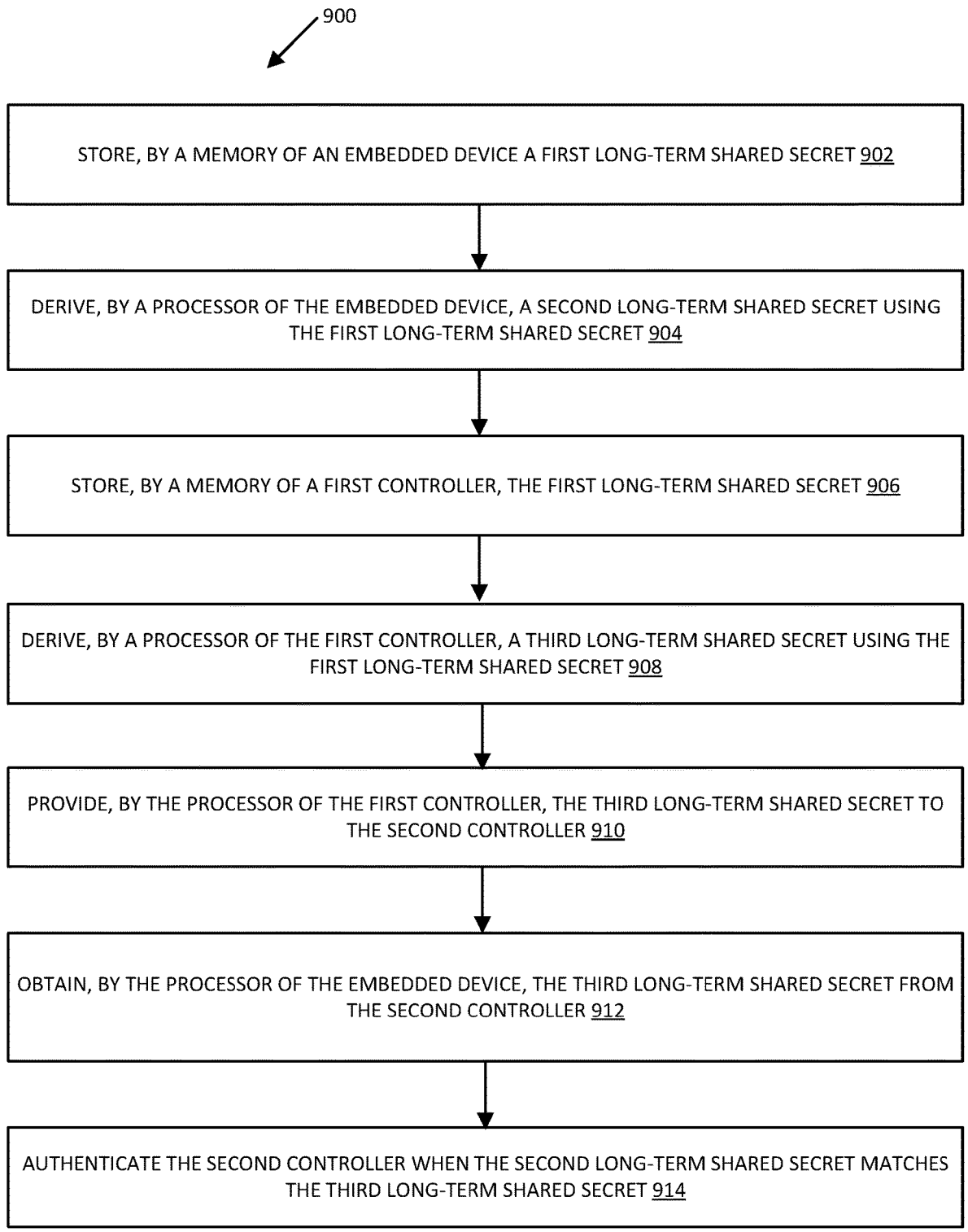
FIG. 9 depicts aspects of an identification and authentication method having a long-term shared secret, in accordance with various embodiments.

Thus, with reference to FIGS. 1 and 9, a method of identification and authentication 900 including a long-term shared secret is provided. In various embodiments, the embedded device memory 48 of the embedded device 44 may store a first long-term shared secret (block 902). The embedded device processor 46 of the embedded device 44 may derive a second long-term shared secret using the first long-term shared secret (block 904). For example, the embedded device processor 46 may perform mathematical and/or cryptographic operations on the first long-term shared secret to derive the second long-term shared secret. The embedded device processor 46 may derive the second long-term shared secret using the identifier of the second controller 28 and independently of any derivation of the third long-term shared secret by the first processor 16 of the first controller 10 discussed later below. The embedded device processor 46 may derive the second long-term shared secret using an identifier of the second controller 28 including a Bluetooth Low Energy (BLE) Media-Access-Control (MAC) address or a nonce.

Additionally, the first memory 12 of the first controller 10 may also store the first long-term shared secret (block 906) so that both the first controller 10 and the embedded device 44 have the first long-term shared secret. The first processor 16 of the first controller 10 may derive a third long-term shared secret using the first long-term shared secret (block 908). For example, the first processor 16 may perform mathematical and/or cryptographic operations on the first long-term shared secret to derive the third long-term shared secret.

The processor of the first controller 10 may provide the third long-term shared secret to the second controller 28 (block 910). For instance, the processor of the first controller 10 may utilize the first network access device 14 to communicate with a second network access device 32 of the second controller 28 via a first communication channel 50 and/or a second communication channel 52. The first processor 16 of the first controller 10 may be configured to derive the third long-term shared secret using an identifier of the second controller 28 including a Bluetooth Low Energy (BLE) Media-Access-Control (MAC) address or a nonce.

The embedded device processor 46 of the embedded device 44 may obtain the third long-term shared secret from the second controller 28 (block 912). Thus, the embedded device 44 may have data representative of the third long-term shared secret and may also have data representative of the second long-term shared secret, both of which are derived from the first long-term shared secret. Consequently, the embedded device 44 may authenticate the second controller 28 when the second long-term shared secret matches the third long-term shared secret (block 914).

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. An identification and authentication system comprising:
   a plurality of controllers including a first controller having a first device certificate and a second controller having a second device certificate, the first device certificate having a first user identifier and a first set of device control privileges, and the second device certificate having a second user identifier and a second set of device control privileges that is different from the first set of device control privileges; and
   an embedded device including:
      an embedded device memory; and
      an embedded device processor configured to:
         obtain, from the first controller, the first device certificate;
         obtain, from the second controller, the second device certificate;
         extract, from the first device certificate, the first user identifier and the first set of device control privileges;
         extract, from the second device certificate, the second user identifier and the second set of device control privileges;
         compare the second user identifier with the first user identifier to authenticate access to the embedded device for the second controller without connectivity to a server;
         determine whether the second user identifier within the second device certificate is the same as the first user identifier within the first device certificate; and
         allow or prevent access to the embedded device by the second controller based on the determination and the extracted second set of device control privileges.

2. The identification and authentication system of claim 1, wherein the first controller includes:
   a first memory configured to store a first application;
   a first user interface configured to receive the first user identifier and a first user password;
   a first network access device configured to communicate with a server or the embedded device; and
   a first processor coupled to the first user interface and the first network access device and configured to:
      send the first user identifier and the first user password to the server,
      obtain, from the server, the first device certificate, and
      send the first device certificate to the embedded device.

3. The identification and authentication system of claim 2, wherein the second controller includes:
   a second memory that is configured to store a second application, wherein the second application is a limited functionality application or a view-only application and the first application is a fully-functional application that has more privileges than the limited functionality application or the view-only application;
   a second user interface that is configured to receive the second user identifier and a second user password, wherein the second user identifier is the same as the first user identifier;
   a second network access device configured to communicate with the server or the embedded device; and
   a second processor coupled to the second user interface and the second network access device, wherein the second processor is configured to:
      send the second user identifier and the second user password to the server,
      obtain, from the server, the second device certificate associated with the second controller, wherein the second device certificate includes the second user identifier and the second set of device control privileges that is different from the first set of device control privileges, and
      send the second device certificate to the embedded device.

4. The identification and authentication system of claim 1, wherein the embedded device memory is configured to store the first device certificate.

5. The identification and authentication system of claim 4, wherein the embedded device processor of the embedded device is configured to:
   determine that the second user identifier is the same as the first user identifier;
   obtain the second set of device control privileges from the second device certificate;
   authenticate access to the embedded device for the second controller without connectivity to a server;
   allow access to the embedded device by the second controller based on the second set of device control privileges; and
   reject or accept commands from the second controller based on the second set of device control privileges.

6. The identification and authentication system of claim 1, wherein the embedded device processor of the embedded device is configured to prevent access to the embedded device by the second controller when the second user identifier is different from the first user identifier.

7. The identification and authentication system of claim 1, wherein the server is configured to:
   obtain the first user identifier from the first controller when a user logins into a first application on the first controller and the second user identifier from the second controller when the user logins into a second application;
   generate the first device certificate including binding the first user identifier and the first set of device control privileges to the first device certificate and based on a type of application requesting the first device certificate;
   generate the second device certificate including binding the second user identifier and the second set of device control privileges to the second device certificate and based on a type of application requesting the second device certificate;
   digitally sign the first device certificate and the second device certificate using a server signing key;
   issue the first device certificate to the first controller when the first user identifier and a first user password are authenticated; and issue the second device certificate to the second controller when the second user identifier and a second user password are authenticated.

\* \* \* \* \*